United States Patent [19]
Massie

[11] Patent Number: 5,891,690
[45] Date of Patent: Apr. 6, 1999

[54] ADENOVIRUS E1-COMPLEMENTING CELL LINES

[76] Inventor: Bernard Massie, 1975, LeRoyer, Laval, Québec, Canada, H7M 2S8

[21] Appl. No.: 638,149

[22] Filed: Apr. 26, 1996

[51] Int. Cl.$^6$ .............................. C12N 5/10; C12N 15/86; C12N 15/87

[52] U.S. Cl. ........................................ 435/172.3; 435/371

[58] Field of Search .................................... 435/371, 325, 435/366, 320.1, 172.3; 514/23.72

[56] References Cited

FOREIGN PATENT DOCUMENTS

WO 94/28152  12/1994  WIPO .

OTHER PUBLICATIONS

Lochmüller, H. et al., 1994, Human Gene Therapy 5:1485–1491.
Imler, J.–L. et al., 1996, Gene Therapy 3:75–84.
Acsadi, G. et al., 1995, J. Mol. Med. 73:165–180.
Graham, Frank L. et al., 1991, Methods in Molecular Biology 7:109–128.
Massie, Bernard, 1988, BioTechniques, vol. 6, No. 7, pp. 616–629.
Imler, J–L et al., 1995, Gene Therapy 2:263–268.
Schaak, Jerome et al., 1995, Journal of Virology, vol. 69, No. 6, pp. 3920–3923.
Babiss, Lee E. et al., 1983, Journal of Virology, vol. 46, No. 2, pp. 454–465.
Acsadi, Gyula et al., 1994, Human Molecular Genetics, vol. 3, No. 4, pp. 579–584.
Zabner, Joseph et al., 1993, Cell, 75:207–216.
Mittereder, Nanette et al., 1994, Human Gene Therapy 5:717–729.
Boucher, Richard C. et al., 1994, Human Gene Therapy 5:615–639.
Engelhardt, John F. et al., 1993, Nature Genetics 4: 27–34.
Trapnell, Bruce C. et al., 1994, Current Opinion in Biotechnology 5:617–625.
Wilmott, Robert W. et al., 1996, Human Gene Therapy 7:301–318.
Massie, Bernard et al., 1995, Biotechnology 13:602–608.
Graham, F.L. et al., 1977, J. Gen. Virol. 36:59–72.
Bett, Andrew J. et al., 1994, Proc. Natl. Acad. Sci. USA 91:8802–8806.
Gunning, Peter et al., 1987, Proc. Natl. Acad. Sci. USA 84:4831–4835.
Mulligan, Richard C., 1993, Science 260:926–932.
Sambrook et al., 1989, Cold Spring Harbor Laboratory Press, pp. 21–104.

*Primary Examiner*—Johnny F. Railey, II

[57] ABSTRACT

The present invention relates to adenovirus (Ad) E1-complementing cell lines which significantly reduce the presence of replication competent Ad (RCA) and can serve for the large scale production of infectious E1-deleted adenoviral particles that may be used for the treatment human patients as for example in gene therapy. As well the invention relates to a method for the large scale production of recombinant infectious adenoviral particles harboring an exogenous sequence of interest and to a RCA-free stock of infectious adenoviral particles. The invention further relates to a recombinant vector for transfecting an eukaryotic cell line in order to construct Ad E1-complementing cell lines which significantly reduce the presence of RCA and to a method therefor.

2 Claims, 2 Drawing Sheets

ADENOVIRUS E1-COMPLEMENTING CELL LINES

FIELD OF THE INVENTION

The present invention relates to the introduction of exogenous genetic sequences into cells, cell lines or organisms, and to gene transfer and gene therapy. The invention further relates to defective adenoviral vectors and E1-complementing cell lines. More specifically the present invention relates to adenovirus (Ad) E1-complementing cell lines which significantly reduce the presence of replication competent Ad (RCA) and can serve for the large scale production of E1-deleted Ad vectors that may be used for the treatment of human patients. As well the invention relates to a method for the large scale production of recombinant Ad harboring an exogenous sequence of interest.

BACKGROUND OF THE INVENTION

Therapeutic strategies in various diseases include: nonspecific measures to mitigate or eliminate a cell dysfunction and prevent cell death; replacement of a missing or malfunctioning protein; introduction of functional nucleic acids (RNA or DNA) into cells to replace a mutated gene and introduction of novel genetic constructs to alter a cellular function. Advances in DNA technology have had a major impact on each of those therapeutic possibilities and nucleic acid transfer into diseased cells appears by far the most promising modality (Mulligan 1993, Science 260:926–932).

Viral vectors permit the expression of exogenous genes in eukaryotic cells, and thereby enable the production of proteins which require post-translational modifications unique to animal cells.

The wealth of information accumulated on adenoviruses over the last decades, has promoted them at the forefront of the gene therapy or immunization fields. Several features of adonoviruses make them attractive as gene transfer tools: (1) the structure of the adenoviral genome is well characterized; (2) large portions of viral DNA can be substituted by foreign sequences; (3) the recombinant variants are relatively stable, (4) the recombinant virus can be grown at high titer; (5) no human malignancy is associated with adenovirus; and (6) the use of attenuated wild-type adenovirus as a vaccine is safe.

Ad ate thus considered as very good vector candidates for in vivo gene transfer. Generally, such vectors are constructed by inserting the gene of interest in place of essential viral sequences such as E1 sequences (Berkner 1988 BioTechniques 6:616–629; Graham et al., 1991, Methods in Molecular Biology, 7:109–128, Ed: Murcy, The Human Press Inc.). This insertion results in an inactivation of the Ad since it can no longer replicate, hence the term replication-defective Ad. In order to propagates such vectors must be provided with the deleted element, (i.e. E1 proteins).

The elucidation of the nucleotide sequence of many Ad subtypes has enabled a precise characterization of the genomic organization thereof. The nucleotide sequence of human Ad5 is available from GenBank under accession number M73260. In simplistic terms adenoviruses comprise: (1) two inverted terminal repeats (ITR) at each end (5' and 3') which are essential for viral replication; (2) the early region 1 (E1) containing the E1A and E1B regions, both indispensible for replication, E1A and E1B are also required for complete transformation of various rodent cell lines, and polypeptide IX (pIX) which is essential For packaging of full-length viral DNA; and (3) the E2, E3 and E4 regions, with E3 being dispensable for replication (reviewed in Acsadi et al., 1995, J. Mol. Med. 73:165–180).

Recently, human Ad serotypes 2 and 5 have been used as vectors for efficient introduction of genes into several cell types both in vitro and in vivo (reviewed in Trapnell et al., 1994, Current Opinion Biotech. 5: 617–625; and Acsadi et al., 1995, J. Mol. Med. 73:165–180). Several factors need to be taken into consideration during the generation of Ad recombinants, among them is the impaired growth characteristics of some of them ( Imler et al., 1995 Gene Ther. 2:263–268; Massie et al., 1995 Bio/Technol. 13:602–608; and Schaack et al., 1995 J. Virol. 69: 3920–3923) which complicate the screening, propagation and production of high quality recombinant viral stocks with high titers (more than $10^{11}$ pfu/ml). Recently, critical issues relating to the characterization of such Ad vectors for gene therapy were reviewed in relation to clinical trials of the cystic fibrosis gene therapy (Engelhardt et al., 1993 Nature Genetics 4:27–34; Zabner et al., 1993 Cell 75:207–216; Boucher et al., 1994 Human Gene Ther. 5:615–639; Mittereder et al., 1994 Human gene Ther. 5:717–729; and Wilmot et al., 1996 Human Gene Ther. 7:301–318). Presently, a number of human clinical trials making use of Ad recombinants for the treatment of diseases like cystic fibrosis, Duchenne muscular dystrophy, and cancer, have started or are being considered (Lochmüller et al., 1994 Hum. Gene Ther. 5: 1485–1491). Potential sites for the insertion of a gene of interest in the recombinant Ad vectors comprise the E1 or E3 regions (i.e. E1+E3-deleted Ad recombinants) or the region between the end of the E4 and the beginning of the 3' ITR sequences. The majority of in vivo gene transfer experiments and human trials have been carried out using E1- and E3-deleted human type 2 or 5 adenoviruses. As alluded to above, E3-deleted recombinants are replication competent E1-deleted recombinants however, are unable to replicate and the missing E1 gene products are provide in trans by the E1-complementing cell line 293 (Lochmüller et al., 1994 Hum. Gene Ther. 5: 1485–1491). The 293 cells were established by stable transfection of a human embryonic kidney cell with adenoviral (human type 5) DNA containing the full length E1 region. The maximum deletion of up to 2.9 kb in the E1 region leaves intact the ITR sequence, the packaging signal at the left and of the adenoviral DNA (188–358 bp) and the pIX coding region (starting at 3507 bp). A useful E3 deletion was made by deletion of a 1.9 kb Xba I fragment (79 and 85 mu). These combined E1 and E3 deletions allowed for inserting approximately 7 kb of foreign DNA sequences in this first-generation recombinant. Extensions of the deletion in the E3 regions further increased the insert capacity to 8 kb, which meets the size requirements for most of the gene therapeutics (Bett et al., 1994 Proc. Natl. Acad. Sci. 91:8802–8806).

It is important to note that the recombinant Ad produced for clinical use have all been obtained using 293 cells (Graham et al., 1977, J. Gen. Virol. 36:59–72). Until the present invention, 293 cell line was the only available complementation cell line which efficiently expressed E1A and E1B RNAs and proteins. Unfortunately, it hats been documented that replication competent, also termed "revertant" virus can appear during multiple passages of the E1- and E3-deleted recombinant Ad in 293 cells, and eventually outgrow the original recombinant in large scale preparations (Lochmüller et al., 1994 Hum. Gene Ther. 5: 1485–1491). The E1 region is acquired from the 293 cells (and its derivatives) by homologous recombination at a very low frequency, but the E1-positive revertants seem to have a growth advantage with respect to their E1-negative counterparts. The presence of these revertants could thus jeopardize the safely of human gene therapy trials, especially when one considers the number of infectious viral particles required in certain applications. Experiments performed with mouse muscle have taught the use of of $2 \times 10^9$ virus particulars to transduce more than 80% of the muscle fibers, since a human muscle is 2500 times larger, that would translate in the use of approximately $10^{12}$–$10^{13}$ viral particulars to inject only one human muscle. Supposing the presence of as little as 1/10 particles of E1+ revertants, in the stock, $10^3$–$10^4$ replication-competent particules would be injected in the muscle. It is clear that such an approach would fail to satisfy regulatory agencies.

Indeed, the 293 cells have been deemed "not suitable for large scale production of clinical grade material since batches are frequently contaminated with unacceptably high levels of replication competent adenovirus (RCA) arising through recombination" (Imler et al., 1996 Gene Ther. 3: 75–84). It should be stressed that the same authors have reported that numerous attempts to construct stable and efficient E1-complementing cell lines have failed and is therefore not a trivial task. In an attempt to solve this problem of RCA generation (Imler et al., 1996 Gene Ther. 3: 75–84) produced an E1-complementing cell line by stably transforming human lung A549 cells with E1 sequences containing the E1A, E1B and pIX regions. Novel A549 E1-complimenting cell lines were obtained which express high levels of E1 RNA and proteins. Strikingly however, the authors were unable to detect E1B protein expression in any of the A549 clones analyzed whether or not they produce high level of E1B RNA. Thus, the presence of a functional genetic unit does not necessarily predict that upon stable integration in the host, it will give rise to the expected proteins. It is also reported therein that the A549 clones, testing positive for infection with E1-deleted Ad vectors, showed a transformed phenotype and that the amplification yields therewith are significantly lower than those obtained with 293 cells. Unfortunately, the generation of RCA with these A549 cells was not assessed. It should be noted that in the Imler et al., constructs, a significant overlap between the complementing element and the defective adenoviral vector occurs at the 3' end of the E1 region (approximately 700 bp). It follows that this overlap significantly increases the probabilities of homologous recombination and hence of the production of E1+ revertants. A disclosure of defective Ad vectors for the expression of exogenous nucleotide sequences in a host cell or organism, as well as vectors for the construction of E1-complementing cell lines, along the same lines is also found in the French publication to Imler et al., WO94/28152. However, this document fails to give an assessment of the yield of production of recombinant Ad by the complementation cell line, of the expression of the different adenoviral transcripts and proteins by the complementing cell line, and very importantly of the presence or absence of RCA during the production process leading to the obtention of the stock of defective Ad harboring the exogenous sequence of interest. It should be noted that WO94/28152 claims to diminish the problem of RCA production by deleting the 5' ITR (a non-substantiated declaration).

There still remains a need for the description of an E1-complementing cell line which combines at least one of the following properties: it expresses E1A and E1B proteins; it minimizes or abrogates the production of E1+ revertants; it is substantially as efficient as 293 or its derivatives in producing recombinant Ad; and it does not show a transformed and rounded phenotype. It would thus be advantageous to be provided with such E1-complementing cell lines which are efficient for the large scale production of E1-deleted Ad vectors devoid of RCA.

All of the above-cited citations are herein incorporated by reference.

SUMMARY OF THE INVENTION

An object of one aspect of the present invention is therefore to provide an E1-complementing cell line which satisfies at least one of the following properties: (1) it expresses functional E1A and E1B proteins; (2) it minimizes the production of E1+ revertants; (3) it is substantially as efficient as 293 or its derivatives in producing infectious recombinant Ad; and (4) it does not show a transformed and rounded phenotype.

Another object of one aspect of the present invention is to provide a method for the large scale production of E1-defective recombinant Ad which minimizes the production of RCA.

An additional object of one aspect of the present invention is to provide a recombinant adenovirus construct for the establishment of an E1-complementing cell line in accordance with the present invention.

Yet another object or one aspect of the present invention is to provide a therapeutic use of an E1-complimenting cell line in accordance with the present invention.

A further object of one aspect of the present invention is to provide a method of treatment by which a therapeutically or prophylactically efficacious quantity of a recombinant Ad, produced in an E1-complementation cell line in accordance with the present invention, or an E1-complementation cell line in accordance with the present invention harboring a recombinant Ad is administered to a patient in need of such a treatment or prophylaxy.

More specifically, in accordance with the present invention, there is provided an adenovirus (Ad) E1-complementing cell line having a stably integrated complementation element comprising a portion of the Ad E1region covering the E1A gene and the E1B gene but lacking the 5' inverted terminal repeat (ITR), the packaging sequence, and the E1A promoter; the E1A gene being under control of a first promoter element and the E1B gene being under control of a second promoter element, the stably integrated complementation element giving rise to functional E1A and functional E1B proteins, whereby the stably integrated complementation element complements in trans a defective adenoviral vector and does not generate replication competent adenovirus (RCA) produced by homologous recombination between said defective adenoviral vector and said complementing element at a detectable level.

In accordance with the invention, there is also provided a method for large scale production of infectious E1-defective adenoviral particles comprising: a) transfecting an E1-defective adenoviral vector into an E1-complementing cell line to obtain plaques; b) screening the plaques to identify plaques positive for E1-defective adenovirus (Ad); c) submitting the E1-defective Ad of b) to at least two rounds of plaque purification by infection into an E1-complementing cell line to obtain substantially pure infectious E1-detective adenoviral particles, and d) scaling up production of the substantially pure infectious E1-detective particles of c) by infecting an E1-complementing cell line and growing the cell line to obtain a concentrated stock of infectious E1-defective adenoviral particles, wherein in at least one of steps a), b), c), and d), the E1-complementing cell line of claim 1 is used, thereby minimizing the production of RCA in the concentrated stock of E1-defective Ad infectious particles obtained in d). In addition there is provided a RCA-free stock of defective adenoviral vector produced in accordance with the above-recited method.

In accordance with the present invention, there is also provided a recombinant vector for constructing an Ad E1-complementing cell line in accordance with the present invention and a method of producing an Ad E1-complementing cell line comprising: a) transfecting a euaryotic cell line with a recombinant vector according to the present invention; b) selecting a cell having stably integrated the complementation element; and c) selecting the cell of b) expressing functional E1A and E1B protein selecting the cell of b) expressing functional E1A and E1B proteins and complementing an E1-defective adenoviral vector so as to yield of infectious E1-defective adenovirus particles while avoiding the generation of a detectable level of RCA.

BRIEF DESCRIPTION OF THE DRAWINGS

Having thus generally describe the invention, reference will now be made to the accompanying drawings, showing by way of illustration a preferred embodiment thereof, and in which.

Figure 1:
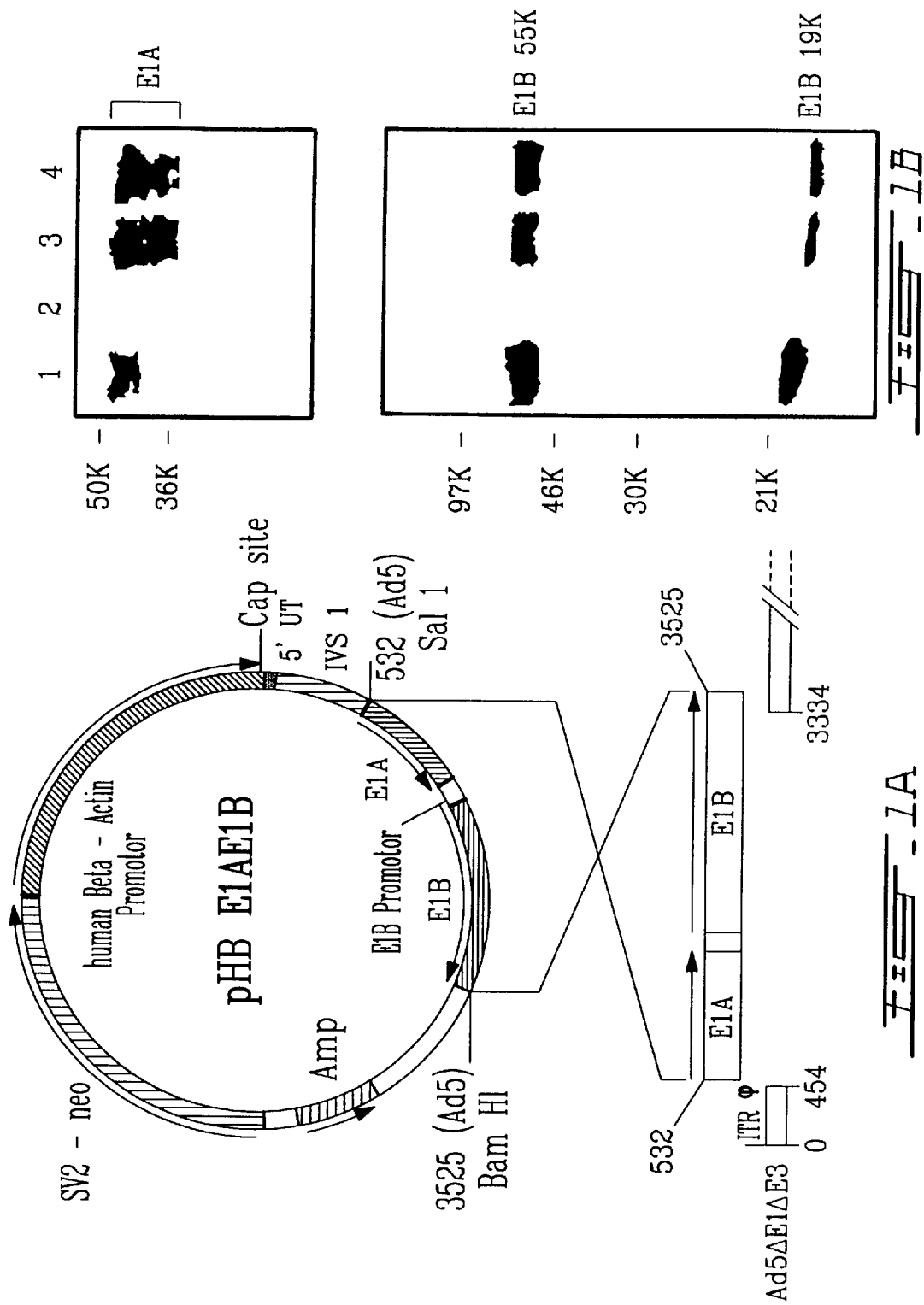
FIG. 1 shows the A 549-AdE1-complementing cell lines; in A is shown a schematic representation of pHβE1AE1B which was used to construct the A549 E1-complementing cell lines, as well as a comparison of the overlap between the sequence thereof and that of the defective adenovirus (Ad5 ΔE1ΔE3); in B is shown immunoblots of A 549 cell lines probed with antibodies to E1A (45K) and E1B (19 kDa and 55 kDa) proteins; lanes 1, 293 control lanes 2, A549 control; lanes 3, BMAdE1-78; and lanes 4 BMAdE1-220.

Other objects, advantages and features of the present invention will become more apparent upon reading of the following non restrictive description of preferred embodiments with reference to the accompanying drawings which are exemplary and should not be interpreted as limiting the scope of the present invention.

DESCRIPTION OF THE PREFERRED EMBODIMENTS

The present invention relates to E1-complementing cell lines which can complement E1-defective adenoviral vectors while significantly reducing the presence of E1+ revertants which have become replication competent (RCA) through recombination with the adenoviral sequences present in the E1-complementing cell line. The minimizations if not the total abrogation of RCA, is crucial if the adenoviral vector harboring an exogenous genetic sequence is to be used in human therapies such as gene therapy. It should be understood that PCR analysis is not sensitive enough to assess the level of purity of an infectious viral stock warranted by the regulatory agencies. The detection of RCAs is thus generally based on tedious plaque assays. The limit of detection of RCA currently available to the skilled artisan is approximately between one RCA per $10^7$ to $10^8$ (perhaps $10^9$) infectious particles. Preferably, the number of RCA in the final adenoviral infectious stock should be inferior or equal to approximately one RCA per $10^9$ infectious particle and especially preferably inferior or equal to approximately one RCA per $10^{10}$ infectious particles.

According to the present invention, when relating to adenoviral vectors, adenoviral sequences, it should be understood that they can be derived from a natural or wild type adenovirus or preferably from a canine, avian or human adenovirus, more preferably a human adenovirus of type 2, 3, 4, 5 or 7 and especially preferably a human adenovirus type 5 (Ad5). In the preferred embodiments described herein, Ad5 was used and the nucleotide positions referred to are taken from the nuclcotide positions 532–3525 as described in GenBank under the reference N° M73260.

It should also be understood that numerous E1-defective adenoviral vectors are encompassed by the scope of the present invention. One of the crux of the invention lying in a minimization of the formation of RCA, a particular E1-defective adenoviral vector should be chosen so as to minimize the presence of homologous sequences between the defective adenoviral vector and the complementing element stably integrated into the genome of the E1-complementing cell line chosen. It will be understood that the complementing cell line should provide the essential elements lacking in the Ad-defective vector used. Defective adenoviral vectors contemplated within the scope of the present invention include without being limited thereto, vectors which comprise in the 5' to 3' direction, the 5' ITR, the packaging sequence, the E2 region, the E4 region the 3' ITR as well as the Major Late transcript region. Since the E3 region is dispensable for replication, that region can be deleted from the Ad vector thereby permitting the insertion of a larger exogenous genetic sequence therein. In a preferred embodiment, the defective adenoviral vector used is Ad5 ΔE1 ΔE3. It is also contemplated that a defective adenoviral vector having additional deletions in essential regions (such as E2 and/or E4) can also be used with the cell lines of the present invention, provided that all defective elements thereof are complemented. For example E2 and/or E4 could be supplied in the E1-complementing cell lines of the invention by a cotransfection of the defective Ad with a vector providing the lacking essential element(s), thereby complementing all the replication defects of the chosen defective adenoviral vector. The term viral "particle" is well known in the art.

The terms "deletion or deleted" should be understood to mean the removal of at least one nucleotide from the targeted region. As well, this deletion can be continued or discontinued. Deletions which remove large portions of the targeted regions are preferred over small deletions, since they diminish the possibility of homologous recombination between the defective adenoviral vector and the complementation element stably integrated in the chromosome of the complementing cell line. The deletion can be a partial or total deletion of the targeted region.

The defective adenoviral vectors to be used according to the present invention arc incapable of replication but gain the capability of replication and encapsidation in the complementing cell line which supplies the defective products in trans. This generates an adenoviral particle which is still defective, since it is incapable of replicating in an autonomous fashion in a cellular host but is nevertheless infectious since it can deliver the vector to the host cell it inflects.

The term "exogenous nucleotide sequence" is meant to cover nucleic acids such as coding sequences and regulating sequences which are generally not present in the genome of adenoviral viruses. It is also to be understood that the exogenous nucleotide sequences should have necessary information to be expressed inside the host cell towards which the defective adenoviral vector is ultimately targeted. It is to be understood that the exogenous sequence can also be expressed in the complementing cell line. The exogenous sequences are introduced in the adenoviral vector by the classical techniques of genetic engineering between the packaging sequence in 5' and the 3' ITR. The exogenous nucleotide sequence can contain one or many genetic sequences of interest and preferably the gene(s) of interest have therapeutic or prophylactic potential. Such a gene of interest can code for an antisense RNA or a mRNA which can be translated into a protein of interest. The gene of interest can be a genomic copy, a cDNA or a chimera of both. It can code for a mature protein, a precursor thereof, a protein chimera, a fusion protein, mutant or modified versions of all such proteins. The mutant protein can be obtained by way of mutation, deletion, substitution and/or addition of the nucleotide sequence encoding the initial protein. The exogenous sequence can be natural, genetically engineered, synthesized chemically or combinations thereof.

The gene of interest can be placed under the control of appropriate control elements ensuring the expression thereof in the host cell. The appropriate control elements comprise transcription elements, generally known as promoter elements and enhancer elements (promoter/enhancer elements), and the translation elements. Herein, the terms promoter element and promoter/enhancer elements are used interchangeably in the broad sense as control elements. The promoter/enhancer element controlling the transcription can be either a constitutive or a regulatable or inducible promoter of eukaryotic or viral origin. It can also be the normal control element for the gene of interest Eukaryotic promoter/enhancer elements are well known to the skilled artisan and can be readily inserted by standard genetic engineering practices in front of the gene of interest or modified to suit the proper need thereof. The promoter/enhancer element can also be tissue specific. The promoter/enhancer element include but are not limited to the SV40 early promoter region, the RSV promoter (in the 3' LTR), the TK HSV promoter, the regulatory sequence of the metallothionine gene, tile insuline control region which is active in pancreatic B cells, immunoglobulin gene control region which is active in lymphoid cells, mouse mammary tumor virus control region which is active in testicular, breast, lymphoid and mast cells, and human beta actin promoter. Preferably the promoter/enhancer element controlling E1A is a strong promoter.

Genes of interest which are encompassed by the scope of the present invention are in essence illimited since a skilled artisan can adapt by conventional method the teachings of the present invention to the expression of his own favorite gene of interest. It should be understood that a limiting factor is the packaging limit of the defective adenoviral vector. In any event, without being limited thereto gene of interest includes: growth factors, receptors, for such growth factors or for other molecules as well as for pathogens, suicide genes, factors involved in blood coagulation, dystrophin, insulin, genes involved in cellular transport such as the cyctic fibrosis transmembrane conductance regulator, or the natural resistance associated macrophage protein gene, genes coding for antisense or inhibitors of pathogenic organisms, inhibitors of defective metabolic processes or inhibitors of pathogens, cancer suppressor genes, genes expressing transdominant proteins, genes encoding antigenic epitopes or variable regions from specific antibodies and immunomodulator genes.

It should be understood that the adenoviral vectors of the present invention need not contain only genes or nucleotide sequences having therapeutic or prophylactic potential. Nevertheless the non-limitating applications of the present invention to gene therapy include a targetting of the following tissues: lung, muscles, liver, kidney, spleen, the nervous system and macrophage. Non-limitative examples of diseases for gene therapy include cystic fibrosis, hemophilia and cancer.

The host cell which is to be chosen to eventually become an E1-complementation cell line in accordance with the present invention can be chosen among a variety of eukaryotic host cells by a skilled artisan. Advantageously, it will be a mammal cell line or preferably a human cell line.

The complenentatioLi cell line according to the present invention can be derived from an immortalized cell line or a primary cell line. In accordance with the present invention, one of the crux of which is to minimize the extent of homologous region between the complementation element and the adenoviral sequences in the defective adenoviral vector, the Eukaryotic E1-complementing cell line according to the invention or their derivatives should minimize the formation of E1+ revert ants or RCA. RCA refers to replication competent adenoviruses which are no longer defective for replication and packaging and can therefore infect cells and lead to toxicity and deleterious immunological reactions. Preferably, the E1-complementing cell lines according to the present invention do not yield detectable RCA by PCR analysis and/or plaque assay on non-complementing cell lines such as A549. More preferably, the E1-complementing cell lines according to the present invention yield a number of RCA per number of infectious viral particles which is insufficient to pose a hazard to a patient when a therapeutic or prophylactic dose of adenoviral infectious particles is administered thereto. Especially preferably, the E1-complementing cell lines of the present invention give rise to no RCA.

The cell line to be chosen to become the E1-complementing cell line of the invention should be a pharmaceutically acceptable cell line. The term pharmaceutically acceptable cell line is meant to refer to the fact that this cell line has been characterized (in terms of history and origin) and/or has been used for the production of products destined for human use (production of material for clinical assays or material destined for sale). Such cell lines are available in depositories such as the ATCC. Without being limited thereto, such cell lines include human carcinoma cells A549, human pulmonary cell line MRC5, human pulmonary cell W138, KB cells, Hela cells and 143 cells. Most preferably, the chosen cell line is the A549 cell line. The A549 and 293 cell lines for example, grow in monolayer. Other cell lines are able to grow in suspension which permits an easier scaling up of production since much larger volumes of cells can be grown. The derivative of the 293 E1-complementing cell line, 293S, possesses this advantageous property of growing in suspension instead of on a solid support.

The method used to stably integrate the complementation element can be performed by standard genetic engineering procedures (Graham et al., 1991, Methods in Molecular Biology, 7: 109–128, Ed.: Murey, The Human Press Inc.) and as described by the present invention. The "complementation element" as used herein refers to a nucleic acid element which can in trans, complement tie replication defect of the defective adenoviral vector used. The E1-complementation cell line is thus capable of producing the protein(s) which is necessary for the replication and packaging of the E1-defective adenoviral vector. It should be understood that the complementation element could be mutated by deletion and/or addition of nucleotides, as long as these modifications do not alter the complementation capacity thereof.

In accordance with the present invention, the complementing element, is expressible, and gives rise to tie E1A and E1B mRNAs as well as to the functional E1A proteins (289aa and 243aa) and E1B proteins (19 KDa and 55 KDa). In accordance with a preferred embodiment of the present invention, the E1A promoter enhancer element has been replaced by the human beta-actin promoter, while the E1B enhancer promoter element is the natural E1B promoter. Of course, these elements can be substituted by other types of enhancer promoter elements which are well known to the skilled artisan. In addition, they could be mutated or modified so as to adapt the expression of E1A and E1B to a particular situation. Advantageously, the complementing element comprises a transcription termination signal and a polyadenylation signal, and preferably those of SV40. In a preferred embodiment of the present invention, the complementation element comprises the nucleotide sequence between nucleotides 532 to 3525 of human Ad type 5 as disclosed in Genbank under reference M73260.

The vector of the present invention enabling the construction of the E1-complementing cell line, should comprise the complementing element with the necessary control elements, as well as a selection marker permitting an assessment of the stable integration of the complementation element into the genome of the host cell. Such selection markers include but are not limited to neomycin resistance (G418), hygromycin resistance, phleomycin resistance and puromycin resistance. In another embodiment, the selectable markers could be supplied by a co-transfected vector. It is also possible to synthesize by way of PCR or chemically the nucleotide sequences required to construct an E1-complementing cell line in accordance with the invention. Since it is a preferred embodiment to transfect a cell line with a linear fragment comprising the E1-complementing element, the E1-complementing element (or cassette) need not necessarily be on a vector. Such a cassette could be for example co-transfected with a vector providing a eukaryotic selectable marker which enables stable integration of the complementing cassette in the genome of the transfected cell. This cassette preferably comprises non-E1 region nucleic acid sequences favoring the integration of a functional E1-complementing element.

In a preferred embodiment of the present invention, the selectable marker is SV2-neo. Preferably, the vector used to construct the E1-complementing cell line will also contain a selectable marker and an origin of replication enabling replication and selection in a microorganism. Selectable markers and origins of replication for microorganisms such as bacteria and lower cukaryotes are well known in the art. The former include without being limited thereto antibiotic resistance, auxotrophic markers and the killer gene system. Non-limitative examples of origins of replication include the standard ColE1 type for bacteria and the 2μ for yeast.

It is also within the scope of the invention to use the complementing cell line harboring a defective adenoviral vector which comprises an exogenous sequence of interest, directly by implantation into a patient. For such an embodiment an E1-complementing cell line could be derived from cells taken from the patient, transfected with the defective adenoviral vector containing the exogenous sequence of interest and implanted back into the patient. Thus, the present invention also encompasses a therapeutic or prophylactic use of a vector containing the complementing element, for deriving an E1-complementing cell line, and the E1-complementing cell lines themselves. In addition, E1-complementing cell lines of the present invention can be used in a method for the preparation of the infectious adenoviral particles which can then be administered to a patient. The administration of such infectious particles for a therapy or prophylaxy, are known to those skilled in the art, since such technologies have been used in a clinical trial for the treatment of cyclic fibrosis for example.

The method of preparation of infectious adenoviral particles according to the present invention, is also based on one of the crux of the invention, the minimization of formation or RCA particles. It will thus become apparent, that the cell lines of the present invention offer a significant advantage over the available complementing cell lines which give rise to a significant number of RCA. Since RCA can outgrow the E1-defective adenoviruses, appearance of RCA early in the course of production of the infectious adenoviral particles could negate the using of a stock of these infectious particles for therapy or prophylaxy. It is of course known that in human gone therapy trial, safety issues are of paramount importance. One of the key requirements is the stable purity of the therapeutic Ad recombinant stocks. Thus, the use of E1-complementing cell lines according to the present invention during the course of production of the viral stock, can be of critical importance for the obtention of a stock of infectious particles which can be administered to patients. It will be understood that the protocol for the production of these infectious particles can be adapted in a variety of ways, by using for example only E1-complementing cell lines according to the present invention, or using other available E1-complementing cell lines in different phases of the scaling up procedure as long as the number of passages in a complementing cell line which gives rise to RCA is minimized.

The therapeutic maid prophylactic uses which are envisioned as falling within the scope of the present invention are related to the type of exogenous sequence which is inserted into the defective adenoviral vectors described above. Pharmaceutical compositions in accordance with the present invention can be manufactured by conventional method. In particular, a therapeutically efficacious quantity of a defective adenoviral particle produced in accordance with the present invention or of an E1-complementing cell line harboring such an adenoviral particle will be mixed with a suitable support or carrier. Compositions encompassed by the present invention can be administered by way of aerosol or any other conventional fashion known in the art, in particular by oral, sub-cutaneous, intramuscular, intravenous, intra-peritoneal, intra-pulmonary or intra-tracheal routes. The administration can be in unit dose or repetitive doses with varying intervals in between doses. The administration of the appropriate dose will vary in accordance with different parameters including the individual to be treated, the disease, the type of exogenous sequence harbored by the adenoviral particle and the type of exogenous sequence harbored by the defective adenoviral particle. As a general rule, the health practitioner will adapt the dosage in accordance with those and other parameters.

The emergence of replication-competent E1+ revert ants in stocks of replication-defective Ad recombinants (ΔE1+ ΔE3) which has been demonstrated (Lochmüller et al., 1994 Hum. Gene Ther. 5:1485–1491), is most likely due to a recombinational event, which occurs at very low frequency, between the complementing element and the defective Ad. Although the population of replication-competent Ad is found at very low level in early passages, this population dramatically increases during the cycles of amplification required to produce large Ad stocks for gene therapy experiments (Lochmüller et al., 1994 Hum. Gene Ther. 5: 1485–1491).

The present invention aims at solving this E1+ revertant problem.

MATERIAL AND METHODS

Cells and viruses

293 E1-transformed human embryonic kidney cells (Graham et al., 1991, Methods in Molecular Biology, 7: 109–128, Ed: Murey, The Human Press Inc.), A549, and Hela S3 cells were purchased from ATCC and grown at 37° C. in Dulbecco's modified Eagle's medium (Gibco) supplemented with 10% fetal bovine serum (Hyclone) and 2 mM glutamine (Gibco). 293 and BMAdE1 clones were infected with AdCMVlacZ (Acsadi et al., 1994 Hum. Mol. Gen. 3:579–584) and AdGFP (a recombinant adenovirus expressing green fluorescent protein) at a MOI of 5-10.

Protein analysis

Cells were harvested, washed in PBS and lysed in Laemmli buffer (10% glycerol, 80 mM tris pH 6.8, 2% SDS). Protein concentration was determined by a Lowry's modified method using the De kit™ (Bio-Rad). Proteins were their separated by SDS-PAGE on a NOVEX™ 10 or 12% precast gel (Helixx).

Western blot hybridization

Proteins were transferred to a Hybond™-C nitrocellulose membrane (Amersham) in a Bio-Rad apparatus. Membranes were blocked overnight using 5% milk in TBS, and hybridized with the appropriate antibodies. Washes were carried out with 0.1% Tween-20™ in TBS. Revelation was made by chemiluminescence using the ECL™ kit (Amersham).

In vitro plaque assay with 293 and BMAdE1 cells

Different dilutions of virus (AdCMVIacZ or AdGFP) were plated on $5 \times 10^5$ cells in a 60-mm dish and overlayed with 1% sea-plaque™ agarose (FMC). Plaques were observed between 7 to 14 days after infection, overlayed with Bluo-gal™ (1% sea-plaque™ agarose, 0.3% NP40™, and 0.2% Bluo-gal™ from Gibco) if needed, and counted. The plaques were observed using an inverted fluorescence microscope for the AdGFP infections.

Indirect plaque assay by beta-gal expression in Hela S3 cells

Hela S3 were infected with virus stocks obtained by infecting BMAdE1and 293 cells with AdCMVlacZ. Different volumes of virus were used in order to obtain a value in the linear range of the beta-gal assay. A standard curve was niade with the AdCMVlacZ stock used for tie stock infections.

Beta-gal assay

Beta-galactosidase assays were performed by a chemiluminescent detection technique using the Galacto-Light™ kit (Tropix). Cells were harvested, washed twice with PBS and resuspended in lysis buffer (100 mM $KPO_4$ pH 7.8, 0.2% Triton X-100 ™, 1 mM fresh DTT) at a concentration of $1 \times 10^6$ cells in 100 μL. Reaction buffer (70 μL of Galacton™ in 100 mM $NaPO_4$ pH 8.0, 1 mM $MgCl_2$) was then added to cell extracts (10 μL) in a luminometer cuvette and the cuvette was placed in the luminometer (Berthold) after 1 hour of incubation. 100 μL of Accelerator (10% Emerald enhancer in 0.2M NaOH) were then injected and the sample was counted for 10 seconds. The positive control consisted of 1 μL of beta-galactosidase from Sigma (in 01M $NaPO_4$ pH 7.0, 1% BSA) added Lo a mock cell extract while The negative control was a mock cell extract.

CONSTRUCTION OF pHβE1AEIB

As a first step in the production of E1-complementing cell lines of the invention, an expression vector containing Ad sequences was constructed. The genetic engineering methods used for the construction of the vectors and cell lines of the present invention are well known methods in the arts. Restriction endonucleases and other DNA modifying enzymes were used according to the supplier's recommendations or according to standard protocols such as that of Sambrook et al., (1989 CSH press; the contents of which is heroin incorporated by reference). Transformation of bacteria, purification of plasmids, transfection, and other molecular biology assays were also performed in accordance with known methods such as found in (Sambrook et al., 1989 CSII press). *Escherichia coli* DH5 strain was made competent and transformed plasmid DNA was prepared by the alkaline lysis method and purified by CsCl-ethidium bromide density gradient centrifugation.

Briefly, the plasmid pHβE1AE1B was constructed by subcloning the 3.0 kb genomic DNA of Ad5 E1region (532–3525) as a Sall-BamH1 fragment into the Sall-BamH1 cloning sites of the pHβApr-1-neo expression vector. These restriction sites were introduced by site-directed mutagenesis in the plasmid pXC38 which contains the Ad5 E1 region from nt 1-5788 (Xhol) subcloned in pBR322 between EcoRI and Sall (a generous gift of Dr. Phil Branton, McGill University, Montréal). The site-directed mutagenesis was performed lining the Transformer™ site-directed mutagenesis kit from Clonetech Laboratories Inc. (Gunning et al. 1987, Proc. Natl. Acad. Sci. USA 82:4831–4835). pHβE1AEIB (FIG. 1A) thus contains as a complementing element the human Ad5 coding region spanning nucleotides 532 to 3525 (Genebank M73260), which consists in the E1A gene, the E1B promotor, and the E1B gene. The expression of E1A is not controlled by the natural E1A promoter but by the strong constitutive human β-actin promotor. As further shown in FIG. 1A pHβE1AE1B only harbors less than 200 bp overlap with the parental adenoviral genome (3334-3525). Since it does not contain the packaging and Ori sequences (the 5' ITR: 0-350), a recombination, although probabilistically infrequent, between the minimal overlap thereof and the Ad genome of the complementing element in the E1complementing cell line should not give rise to a viable particle, thereby eliminating the problem due to the presence of Ad E1+ revert ants or RCA.

ENGINEERING OF THE BMAdE1 COMPLEMENTING CELL LINES

To construct the BMAdE1 complementing cell lines the A549 (human lung epithelial cells) were transfected with pHβE1AE1B (FIG.1A).

A total of 10 μg of purified pHβE1AE1, previously cut with ScaI, were transfected onto A549 cells, a human lung carcinoma cell line (ATCC, CCL185) using the standard calcium phosphate precipitation technique. It should be understood that various methods of transfection arc well known in the art and that the present invention is not limited to transfection by the calcium phosphate procedure. For example, the vector could be lipofected or electroplated.

INITIAL CHARACTERIZATION OF BMAdE1 CLONES

To determine whether or not the A549 cell lines expressed Ad E1A and E1B functions, after transfection with pHβE1AE1B, they were infected with AdCMVlacZ tat a multiplicity of infection of 5–10 pfu/cell. Seventy-two hours later, cytopathy was apparent and the non-infected controls of the positive cell lines were harvested, lysed, and analyzed on a Western blot (FIG. 1B).

Results show that the expression of the E1B 19K and 55K proteins was not as high in the A549 cell lines as in 293 cells. However, in one of the A549 cell lines there was more E1A proteins than in 293 cells. It is conceivable that the cell lines which were less infected by AdCMVlacZ expressed less E1A and E1B. In other words that there is a correlation between the extent of infection and the expression of E1A and E1B protein from the complementing element.

The expression of adenovirus E1A and E1B products had already been shown in KB cells (Babiss et al., 1983 J. Virol. 46: 454–465). However the KB complementing cell lines of Babiss et al., are similar to 293 cells since the whole E1region, including the 5' ITR and packaging sequences are present in the complementing cell line and therefore does not diminish the RCA problem encountered with 293 cells. In addition, the yields of infectious particles in these cells is generally lower than in that of the reference complementing cell line, the 293 cell line. Consequently, the complementation exerted by the KB complementing cell lines is only partial as compared to 293 cells. The present studies differ from the previous work on two points. Firstly, the expression of E1A products in the present construct is controlled by the stronger human beta-actin constitutive promotor, instead of the SV40 early promotor. This seems to ensure a better expression of the Ad E1proteins. Secondly, no cell lines were identified which only expressed E1A proteins.

VIRAL PROGENY IN SELECTED BMAdE1CLONES

To assess the virus yield of the BMAdE1 clones, different clones were infected with AdCMVlacZ at a multiplicity of infection of 5–10 pfu/cell. The virus stock obtained with this infection was indirectly titered by a beta-gal chemiluminescent assay, the expression of lacZ being considered proportional to the amount of infectious virus (Table 1).

TABLE 1

Ad5CMVlacZ progeny comparison between BMAdE1 clones and 293 cells

| Ad5CMVlacZ | production (PFU[a] per cell) | in cell line: |
|---|---|---|
| 293 | BMAdE1 78–42 | BMAdE1 220–8 |
| 800 | 200 | 800 |

[a]Number of PFU was determined indirectly by β-gal expression in Hcla S3 cells after 48 hours of infection with Ad5CMVlacZ stocks done on 293 and BMAdE1 clones.

Figure 2:
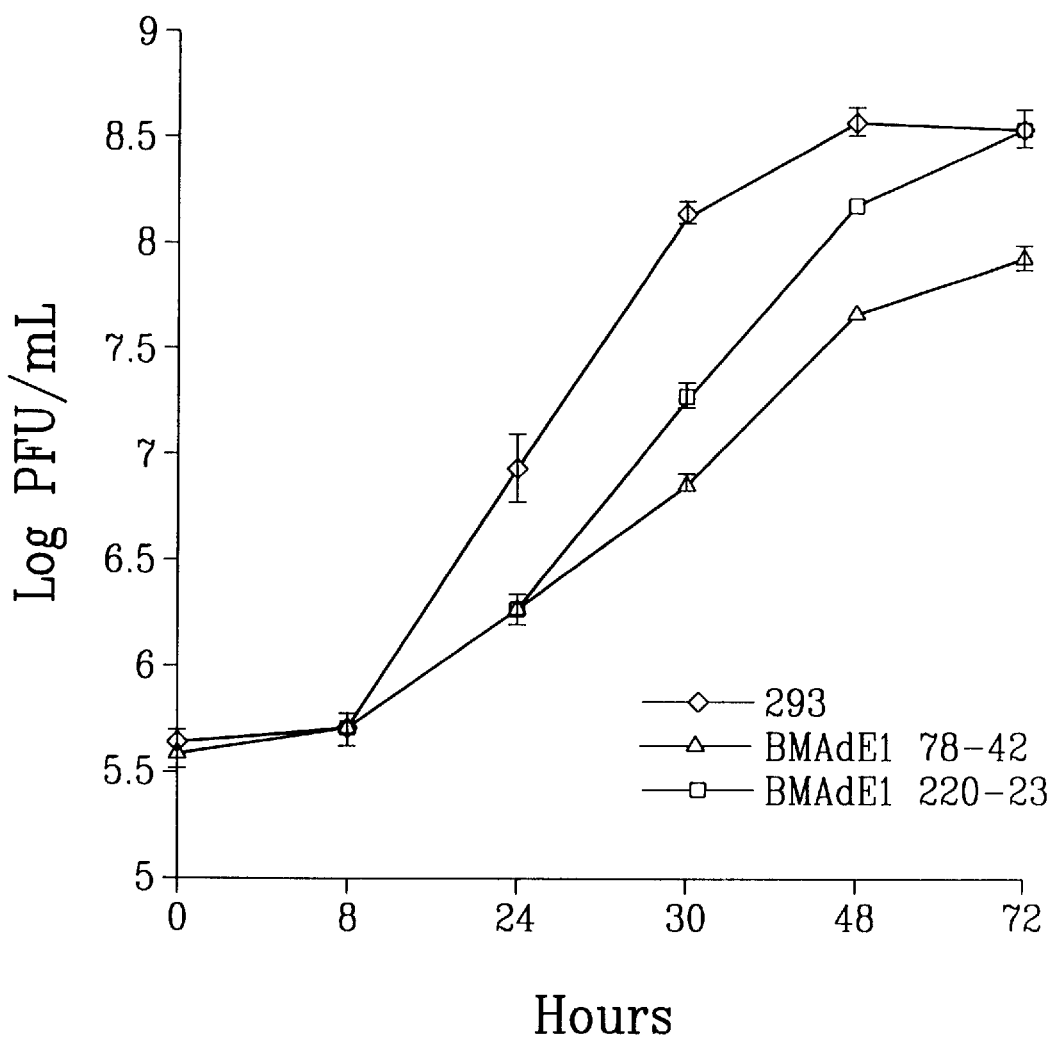
FIG. 2 shows a diagram depicting viral multiplication of Ad5CMVlacZ in BMAdE1 clones compared to 293 cells.

The result show that the expression of lacZ, which reflects the expression of the virus, in the BMAdE1 clones is delayed when comnpared to 293 cells (FIG. 2). Although the viral progeny of the BMAdE1 78-42 clone is four times inferior to that of the 293 cells, the BMAdE1 220-8 clone gives the same amount of infectious viral particules. Thus, in relative terms, the BMAdE1 220-8 complementing cell line complements the E1-defect to the same extent as the 293 complementation cell line.

VIRAL TITRATION WITH THE SELECTED BMAdE1 CLONES

To determine the capacity of the BMAdE1 clones to plaque efficiently, dilutions or an AdGFP stock were plated on BMAdE1 78-42, BMAdE1 220-8, and 293 cells. The plaquing efficiency assessed the quality of the plaques and how easy it is to distinguish and count them following a productive infection. The results are presented in Table 2.

TABLE 2

Viral titers of a AdGFP stock[a] of BMAdE1 clones compared to 293 cells

| AdGFP titer | (PFU/ml) | in cell line: |
|---|---|---|
| 293 | BMAdE1 78–42 | BMAdE1 220–8 |
| $7 \times 10^9$ | $2 \times 10^9$ | $3 \times 10^9$ |

[a]AdGFP stock was made by infecting $5 \times 10^8$ 293 cells. Harvesting was done at 48 hpi, and the pellet was resuspended in 50 ml of medium and frozen/thawed three times.

Titers three and two fold inferior to that obtained with 293 cells were observed with the −78 and −220 clones, respectively.

For the AdGFP infection, the plaques were observed with an inverted fluorescence microscope, thereby allowing a visualization of at least twice the amount of plaques observable with the naked eye. This was confirmed by using bluo-gal™ for AdCMVlacZ infection.

The fact that BMAdE1 220-8 grows more in clusters as compared to BMAdE1 78-42 does not allow the easiest visualization of the plaques with the naked eyes. Nevertheless, BMAdE1 clones can still be used to plaque-purify viruses after co-transfections, since one of the main goals of the present invention is to get rid of the RCAs in virus stocks. In a preferred embodiment, 293 cells could be used for the initial transfection. The scaling up of the production of infectious E1-defective particles would be performed using the complementing cell lines of the present invention, preferably BMAdE1 220, since it produces infectious particles at the same level as 293 cells. The 293 cells could also be used for titering purposes in view of their good plaquing efficiency. A property which is somewhat shared by BMAdE1 78. When the RCA problem is not so acute, the 293S derivative, which grows in suspension, can be used for later stages of the preparation of the infectious particles. The conventional 293 cell line as well as the BMAdE1 cell lines of the present invention all grow in monolayer and hence do not provide the ease of scaling up of cells growing in suspension. When both BMAdE1 and 293 cell lines are used for the preparation of infectious particles it is preferable to use the latter for the late passages, thereby avoiding the expansion of RCAs.

DEPOSITS

The E1-complementing cell lines BMAdE1-78-42 and BMAdE1 220-8 have been deposited at the American Type Culture Collection (ATCC) 10801 University Blvd., Manassas, Va. 20110-2209 under accession numbers CRL-12408 and CRL-12407, respectively.

CONCLUSION

In summary the present invention provides in particular, E1-complementing cell lines which overcome the problem of RCA production and a recombinant vector for constructing such E1-complementing cell lines. These cell lines avoid the emergence of E1+ revert ants during multiple passages and amplification of Ad helper-independent defective vectors. It was herein demonstrated that the BMAdE1-220 cell lines can complement ΔE1Δ3Ad recombinants at the same level as 293 cells. This cell line allows the production of approximately 1000 infectious particles of Ad5CMVlacZ per cell, a value which is comparable to that obtained in 293 cells (Table 1). This is in contrast to the E1-complementing cell lines obtained by Imler et al., (1996 Gene Ther.

3:75–84), which "are able to support replication of E1-deleted adenoviruses, although not as efficiently as 293 cells (Table 1)". Indeed, the best complementing cell line obtained thereby yields approximately 5 fold less infectious particles per cell, and in one case as low as 100 fold less (Imler et al., 1996 Gene Ther. 3:75–84).

The BMAdE1-78 E1-complementing cell line while not being as good a producer of infectious particles as BMAdE1-220 or 293 (producing about 4 fold less per cell), provides however the advantage of showing a less transformed, rounded phenotype than BMAdE1-220, making it a better cell line for plaque purification.

Importantly, the cell lines of the present invention have not been shown to generate RCA during multiple passages. By providing a region of homology of less than 200 bp between the complementing cell lines of the present invention and the E1-defective adenoviral vectors, which is less than previously disclosed cell lines used, the likelyhood of RCA emergence is expected to be lower than that of previously disclosed complementing cell lines. In fact, no RCA is expected to emerge during the production of the stocks of infectious Ad particles using the complementing cell lines of the invention.

Finally, the expression of functional E1B proteins in the complementing cell lines of the present invention is thought to favor expression of viral proteins and lead to superior yields of infectious virus particles per cell. In addition E1B protein expression might diminish the known toxic effects that accompany E1A expression.

The present invention is not to be limited in scope by the recombinant constructs and cell lines exemplified or deposited which are intended as but single illustrations of one aspect of the invention. Indeed, various modifications of the invention in addition to those shown and described herein will become apparent to those skilled in the art from the foregoing description and accompanying figures. Such modifications are intended to fall within the scope of the appended claims.

What is claimed is:

1. An Ad E1-complementing cell line designated BMAdE1-220-8, deposited with the ATCC under accession number CRL-12407.

2. A method for large scale production of infectious E1-defective adenoviral particles:

a) transfecting an E1-defective adenoviral vector into an E1-complementing cell line to obtain plaques;

b) screening said plaques to identify plaques which are positive for E1-defective adenovirus (Ad);

c) submitting said E1-defective Ad of b) to at least two rounds of plaque purification by infection into an E1-complementing cell line to obtain substantially pure infectious E1-defective adenoviral particles; and d) scaling up production of said substantially pure infectious E1-defective adenoviral particles of c) by infecting an E1-complementing cell line and growing said cell line to obtain a concentrated stock of infectious E1-defective adenoviral particles, wherein in at least one of steps a), b), c), and d), said E1-complementing cell line is said Ad E1-complementing cell line of claim 1, thereby minimizing the production of replication competent adenovirus in said concentrated stock of infectious E1-defective adenoviral particles.

* * * * *